United States Patent [19]

Noeller

[11] 4,419,583

[45] Dec. 6, 1983

[54] POLARIZATION FLUOROIMMUNOASSAY WITH PULSED LIGHT SOURCE

[76] Inventor: Hans G. Noeller, 1942 Deerpark Dr. #92, Fullerton, Calif. 92631

[21] Appl. No.: 266,968

[22] Filed: May 26, 1981

[30] Foreign Application Priority Data

May 31, 1980 [DE] Fed. Rep. of Germany ....... 3020730

[51] Int. Cl.³ .................... G01N 21/64; G01N 21/00; G01N 21/01
[52] U.S. Cl. .............................. 250/458.1; 250/461.2; 356/318; 356/417; 436/805; 436/807
[58] Field of Search ....................... 356/317, 318, 417; 250/458, 459, 461, 458.1, 461.2; 424/8

[56] References Cited

U.S. PATENT DOCUMENTS

| | | | |
|---|---|---|---|
| 3,679,309 | 7/1972 | Hiragaki | 356/317 X |
| 4,071,770 | 1/1978 | Shinitzky | 250/461 B |
| 4,076,420 | 2/1978 | De Maeyer | 356/73 |
| 4,115,699 | 9/1978 | Mizuta | 250/461 B |
| 4,133,873 | 1/1979 | Noeller | 424/8 |
| 4,295,199 | 10/1981 | Curry | 250/461.2 X |

OTHER PUBLICATIONS

R. D. Spencer et al., Clin. Chem., 19(8), 838-844, (1973).
G. Weber et al., Jour. Biol. Chem., 241(11), 2558-2561, (1966).
S. R. Popelka et al., Clin. Chem., 27(7), 1198-1201, (1981).

*Primary Examiner*—Sidney Marantz
*Attorney, Agent, or Firm*—Knobbe, Martens, Olson & Bear

[57] ABSTRACT

Fluroroimmunoassay of fluoroescently tagged species using pulsed high intensity light, and single or paired fluorescent detectors, and polarizing the activating radiation and both fluorescent radiation outputs and apparatus for carrying out such assay is disclosed.

3 Claims, 2 Drawing Figures

POLARIZATION FLUOROIMMUNOASSAY WITH PULSED LIGHT SOURCE

FIELD OF THE INVENTION

This invention relates to immunoassays generally and, more specifically, to fluoroimmunoassays of biological species. Still more specifically, this invention relates to an improved and modified polarization fluoroimmunoassay method and apparatus.

BACKGROUND

Numerous biological substances are quantitatively or semiquantitatively determined by immunological methods. Radioimmunoassay (RIA) opened a new generation of trace determination techniques and permitted a degree of sensitivity into the molecular range, not hitherto attainable. RIA techniques are presently being displaced quite extensively, however, nonradioactive determining methods are needed which permit an approximately equal degree of sensitivity, but avoid the problems inherent in handling radioactive materials. One such method is the widely used fluoroimmunoassay, which is well known and is extensively described in the published literature. See, for example, Davis et al, MICROBIOLOGY, 2nd edition, Harper & Row, 1973, pp. 397 et seq.; Cooper, THE TOOLS OF BIOCHEMISTRY, Wiley-Interscience, New York, 1977; and Iesen, IMMUNOLOGY, Harper & Row, 1974.

Fluoroimmunoasay techniques using pulsed light, i.e., a strobe light or photoflash type light, referred to as pulsed fluoroimmunoassay (PFIA), have been described in my U.S. Pat. No. 4,133,873 and my German Patent Application corresponding thereto, No. P 25 23 209.1. PFIA displays numerous advantages as compared with other isotopic and nonisotopic immunoassay methods. The literature has also reported that fluorescent molecules, when excited by polarized light, emit luminous energy which, in its polarization value, decisively depends upon the molecular size of the species which fluoresced. The degree of polarization also depends upon other parameters, such as, for example, the number and type of these molecules, the state of the molecules, i.e., whether or not the molecules are bound at one position or are unbonded to one another, etc. See the foregoing references and Parker, C.W., in Weir, HANDBOOK OF EXPERIMENTAL IMMUNOLOGY, third edition, Volume I, pp. 18.1 et seq.

With the formation of the antigen-antibody complex, the molecular size of the species is changed in all immunological reactions. As a result of this change in size in the immunological reaction, a fluorescent tagged immunological substance undergoes a change in its fluorescence polarization characteristics, i.e., a fluorescent tagged antigen fluoresces differently and, in particular, has a different degree of rotation in its unbound condition as compared with its condition when bound to an antibody. Similarly, a fluorescent tagged unbound antibody behaves differently than the same antibody bound to an antigen.

SUMMARY OF THE INVENTION

The evaluation of the polarization fluorescence of a fluorescent tagged species with respect to the intensity in the various polarization ranges, according to the present invention, allows one to determine the presence and to semiquantitatively determine the amount of an immunological reaction in a very simple manner, even in cases in which the values obtained without polarized light are not taken into consideration and, when this technique is combined according to the present invention with the use of pulsed light sources, as compared with conventional continuous high intensity beam producing sources, allows one to use extremely high intensity pulsed light for the fluorescent excitation of the species to be determined or measured, and allows one to extend the sensitivity of the technique to the very limits of the theoretically possible sensitivity attainable by fluoroimmunoassay techniques. All this is accomplished, according to the present invention, without the sample being damaged, as occurs in conventional techniques through the excessive accompaniment of heat evolution and also without the measured value being influenced in any significant manner as a result of the bleaching effect of continuous fluorescent photoradiation upon the species to be measured.

Accordingly, the present invention comprises, in one feature, apparatus for directing a polarized, high intensity pulse of light into a sample containing fluorescent tagged species and measuring simultaneously the intensity of the fluorescent emitted light seen by two photosensors through two differently (vertically and horizontally) oriented polarizers, so determining directly and quantitatively or semiquantitatively the amount of the bound versus the unbound tagged immunopartner. These principal features of the invention and other features of the invention, including the method and the apparatus and additional features of the present invention are with great particularity described herein.

DESCRIPTION OF THE PREFERRED EMBODIMENT OF THE INVENTION

Figure 1:
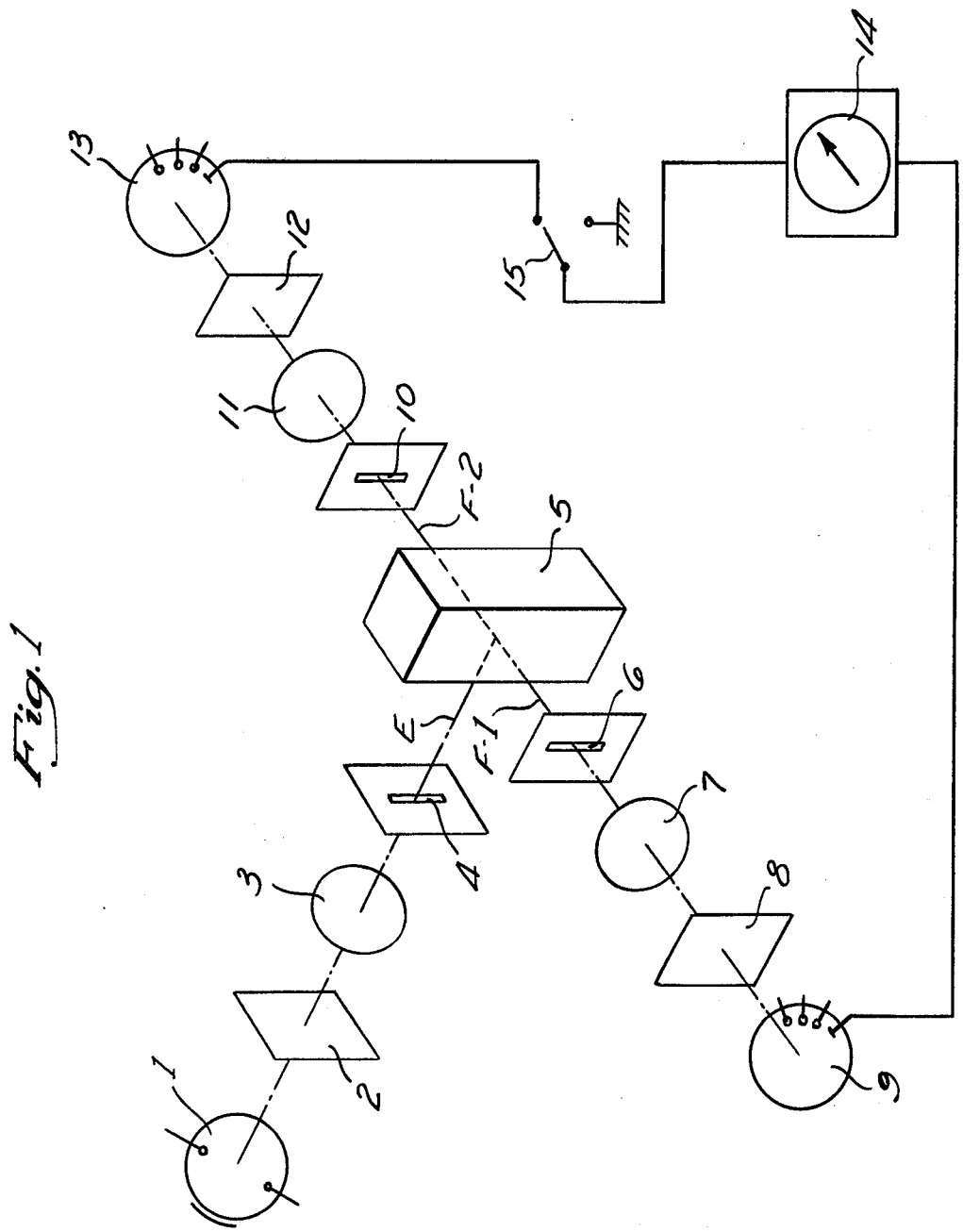
FIG. 1 is a schematic diagram of the apparatus of this invention, and, insofar as individual components are concerned, operates in the manner described in my earlier U.S. Pat. No. 4,133,873, issued June 9, 1979, entitled METHOD OF DETERMINING EXTRACELLULAR ANTIGENS AND ANTIBODIES.

A simple, tested embodiment which exemplifies, but does not limit, the invention, is shown in FIG. 1. This type of apparatus has been used for polarization fluorescence immunoassays according to the present invention.

Referring specifically to FIG. 1, and incorporating by reference the disclosure in my aforesaid U.S. Pat. No. 4,133,873, the excitation light for the apparatus of this invention is provided by a source 1 of pulsed, high intensity light such as is used by conventional cold cathode photoflash units, the most common of which use xenon as the photo-radiating medium.

The light pulse is monochromatized by an excitation filter 2, which, in the simplest case, is simply an interference filter. Any monochromator commonly used in photometry may, however, be used. The pulse light is then polarized by the polarization filter 3 which, again, is of conventional composition and design. Polarizing filters are commonly used in photography and in many scientific applications, and any good quality polarizing filters may be used in this invention. The monochromatized, polarized pulse is then collimated by slit 4 and enters the cell 5 in which the sample containing the fluorescent tagged species is contained. For identification in the drawing, the pulse light beam used for exciting the sample is identified as beam E.

The fluorescent tagged species, when excited by the beam E, emit fluorescence radiation at all angles, and the intensity of such radiation can be measured at any desired angle. However, it is preferred that the measurements be made at 90° to the incidence of the excitation beam in order to minimize background resulting from the beam. Accordingly, as shown in FIG. 1, two fluorescent beams identified as F-1 and F-2 at 90° from the excitation beam and at 180° from each other, are selected. Beam F-1 is passed through a collimating slit 6, in one direction, through a monochromator such as interference filter 7 to select a desired emission wave length, then through a polarization filter 8 and to a photomultiplier 9. The slit, monochromator and polarizer may be of the type described with respect to the corresponding elements in the excitation beam, and the photomultiplier is a conventional photomultiplier used in photometry.

A similar arrangement is provided 180° from fluorescent beam F-1 where fluorescent beam F-2 passes through a slit 10, monochromator interference filter 11, which selects the same emission wave length, then through polarization filter 12 and to a like photomultiplier 13.

The signals given off by the photomultipliers 9 and 13 are compared with one another in an evaluation system 14, generally of the type described in my aforesaid U.S. Pat. No. 4,133,873, and may be indicated by any conventional device such as a meter, indicated as part of a system 14, or may be recorded graphically as is commonly done in photometry.

The switch 15 permits one to turn one of two photomultipliers out of the circuit so that, by appropriate orientation of the polarization angle of the polarizer filter 3, the apparatus can be used as a simple polarization fluorometer and not as a difference fluorometer. Likewise, the polarization filter 3 can be removed from the path F-1 and the apparatus used as a nonpolarizing fluoroimmunoassay device.

In the evaluation system 14, the impedance of the pulse signals from the photomultipliers 9 and 13 can be reduced and matched using conventional impedance matching devices such as unity gain operational amplifiers. The pulse signals can be subsequently transformed into voltage which vary as a function of the pulse energy by an operational amplifier in each circuit serving as an integrator for the energy induced in the photomultiplier by the pulse, i.e., the pulse energy. Integrated voltage is then loaded onto a capacitor, using conventional integrating circuitry and the signal depending voltages present on the respective capacitors, which represent the respective pulse energies and, consequently, the intensity of the polarized fluorescent radiation at the particular wave length emitted by the sample, which are present on the two capacitors are fed through field effect transistor input operational amplifiers to conventional comparison circuitry. Field effect transistor circuitry of the type commonly used is described, inter alia, in my aforesaid U.S. Pat. No. 3,133,873, and is conventional circuitry. The ultimate output is a voltage the magnitude of which is a function of the difference between the signals taken by the two photomultipliers and, consequently, the difference in the intensity of the fluorescence beams F-1 and F-2. The polarization analyzing filters 7 and 11 are, in a typical application of the apparatus and of the method, rotated with respect to one another by 90°. The polarization filter 3 in the excitation beam is suitably affixed in a rotatable manner, e.g., simply mounted loosely to permit rotation, in order to be able to optimize the apparatus in varying applications. Thus, the polarization orientation of the polarizer 3 may be varied at the will of the operator to optimize the desired polarization of the excitation beam E, merely by appropriate filter adjustment.

EXEMPLARY APPLICATIONS OF THE INVENTION

Many potent modern medications have the disadvantage of displaying a biologically effectiveness range of only a small order of magnitude, i.e., they must be administered and kept within any narrow range of concentration, and the biological half life of the medication varies from patient to patient. Thus, it is necessary to maintain nearly continuous controls on the amount of the medication in the blood level of the patient when these medications are used, in order to be able to correct the dosage at the earliest possible time to protect against impending side effects due to too high concentrations or inadequate medications due to too low concentrations in the blood. Such substance include Digoxin, Norpace, Amikacin, Kanamycin and Gentamicin.

An example of the method of this apparatus is given below using Gentamicin as a typical medication which requires some monitoring.

The concentration of Gentamicin in the blood can be determined according to the present invention in a simple manner, quickly, reliably and with the highest degree of precision according to the method described below. A plurality of samples, two ml each, of a solution of fluorescein tagged Gentamicin, of any desired or suitable concentration, in a 0.05 molar Tris buffered solution adjusted to a pH of about 7.1 are treated, respectively, with 50 μl of:

(A) patient serum
(B) Gentamicin free control serum
(C) Control serum with 1 μg Gentamicin/ml
(D) Control serum with 2 μg Gentamicin/ml
(E) Control serum with 4 μg Gentamicin/ml
(F) Control serum with 8 μg Gentamicin/ml
(G) Control serum with 16 μg Gentamicin/ml The samples are then incubated for 10 minutes at room temperature.

Figure 2:
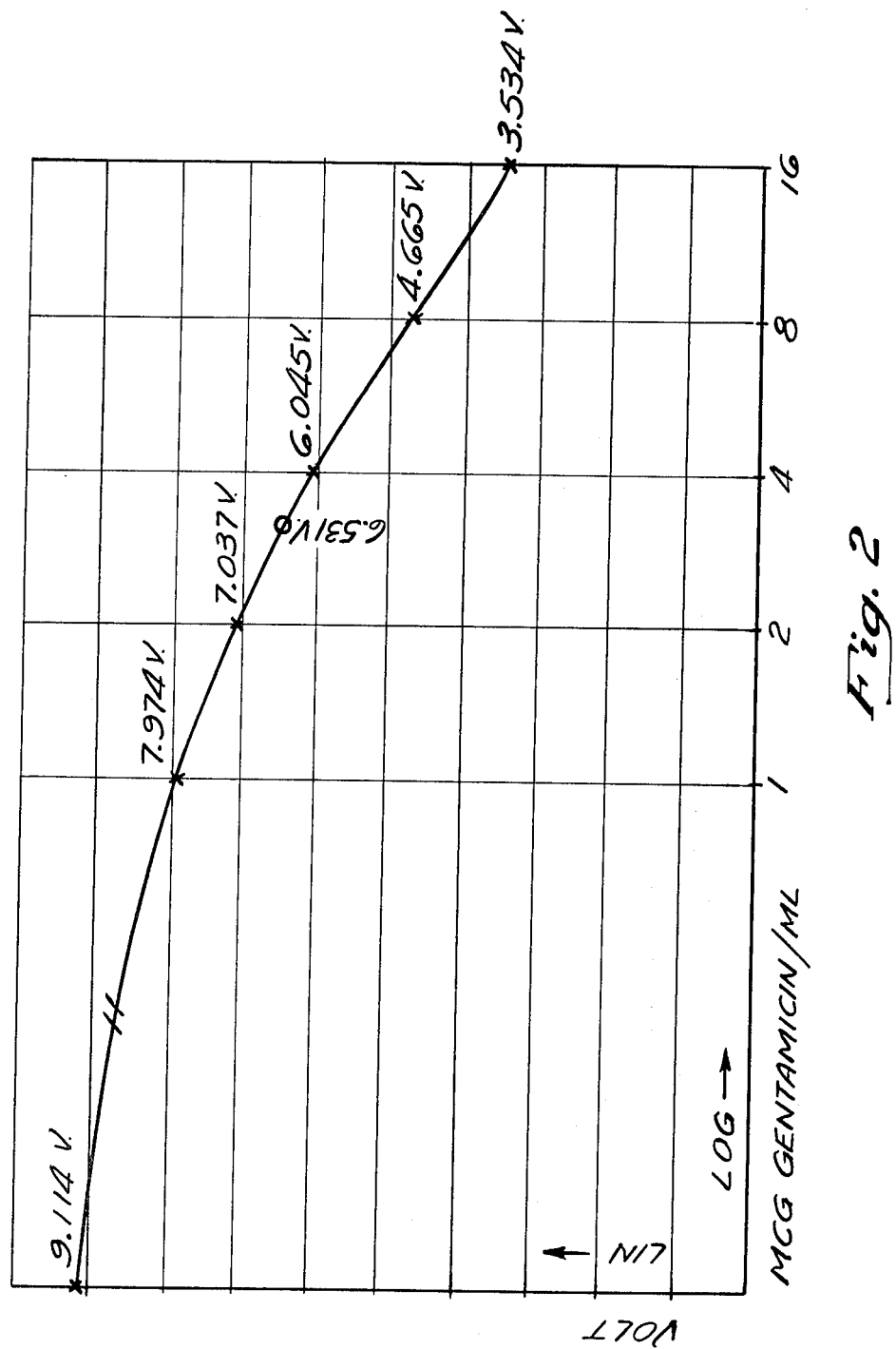
FIG. 2 is a calibration curve typical of that used in the present method, in semilogarithmic scale.

The samples are introduced, one after another, into the measuring cell 5 and the cells placed in the apparatus. One pulse each of the light is introduced into the sample as the excitation energy. The difference in fluorescence as measured through the two measuring systems, concluding with the two photo cells 9 and 13, is then read off from the evaluating device 14. The fluorescence difference value, i.e., the difference in the measured fluorescence according to this method, of the patient's serum is compared with values shown in a standard curve plotted from the data of the control series, samples (B) through (G). A standard curve of this type is shown in FIG. 2. This immediately gives the Gentamicin concentration in the patient's serum in μg Gentamicin/ml of serum.

In the case under discussion, the following values were obtained:

(A) Patient serum, 6.513 V
(B) Control serum 0 μg/ml, 9.144 V
(C) Control serum 1 μg/ml, 7.974 V (D) Control serum 2 µg/ml, 7.037 V
(E) Control serum 4 µg/ml, 6.045 V
(F) Control serum 8 µg/ml, 4.665 V
(G) Control serum 16 µg/ml, 3.534 V FIG. 2 shows the values graphically plotted on semilogarithmic paper. The graphic plotting produces the standard curve. From the standard curve it becomes apparent that the Gentamicin content in the patient's serum is 2.8 µg/ml.

The foregoing is given as an exemplary embodiment of the invention, and does not limit, in any manner, the scope or application of the invention. The present invention may be used, for example, and all immuno complexes which have been labelled with a fluorescent tagged substance and which can be evaluated by means of fluoroimmunoassay methods. This method can be used for the competitive, as well as for the sandwiching immunoassay techniques. Sandwiching or solid substrate fluorescent immunoassay techniques are, of course, well known and are described in my aforesaid U.S. Pat. No. 4,133,873, and also in the other references to herein before and incorporating herein by reference. The present invention is, therefore, of general applicability to fluorescent immunoassay techniques in which there is a difference in polarization fluorescence according to the state of the fluorescent tagged species, e.g., bound versus unbound.

The utilization of the polarization fluorescent immunoassay technique of this invention can be used to identify and prove the existence of as well as to quantitatively determine a concentration of immunological reaction components of small and average sized molecules in cases where the highest degree of sensitivity and precision is required and where great values placed upon easy operation and rapid execution of determinations of this general type.

The necessity of separating bound immuno reaction components from unbound immuno reaction components is one of the greatest disadvantages of all heterogenous immnoassay techniques. This great disadvantage is eliminated in the present case by using the homogenous polarization fluorescence immunoassay apparatus and method as described herein before, in which the molecular size has an influence on the measured signal. This is based upon the fact that, in liquid media, the immunological substances with small molecular sizes are exposed to a much greater extent to the Brownian molecular movement than those with larger molecular sizes. Accordingly, small molecules change their spatial arrangement within the very short time period between fluorescent excitation and emission of fluorescent light as a result of that excitation and, therefore, appear to be less polarized than large molecules which, during the same time period, change their spatial arrangement only a minimal extent and consequently, change their emission polarization orientation only to a minimal extent.

A solution containing small molecules of fluorescent tagged immunological substances which, when viewed under nonpolarized light, shows exactly the same fluorescence characteristics as the solution containing large molecules of the same fluorescent immunological substances when viewed under polarized light. However, the solution containing small molecules of fluorescent tagged immonological substances displays a polarization which is of a small, minimal order of magnitude, as compared with the polarization magnitude of a solution containing large molecules with the same fluorescent tagging. However, as the small molecules combined themselves with other substances as, for example, through an immunological reaction, to form an immuno complex, and consequently become larger, they become far less subject to the Brownian molecular movement and, accordingly, can be easily determined semiquantitatively by measurement of the polarized light emitted therefrom.

The polarization of fluoroimmunoassay according to the present invention has a large number of advantages as compared with the conventional immunoassay methods. Because the pulse light is of such very high intensity and very brief duration, and by reason of a difference measurement of the polarized fluorescence, the background is reduced by several orders of magnitude, as compared with the best conventional fluorescent immunoassay methods available heretofore. This permits a degree of sensitivity comparable to the best prior immunoassay techniques, but with much less effort and with greater reliability.

The polarization fluoroimmunoassay is not afflicted with the dangers and disadvantages resulting from radioisotopes as in the more traditional RIA techniques of the prior art.

The polarization fluoroimmunoassay can be carried out with extremely low expenditures of time and, correspondingly, low monetary expenditures in a quick and efficient manner with the highest degree of precision. The polarization fluoroimmunoassay method of this invention can also be used without difficulty for making kinetic determinations, thus making it possible quickly and accurately to determine the reaction velocity of the immunological reaction of interest.

One of the great advantages of the polarization fluoroimmunoassay of this invention, as compared with most conventional immunological assays, is that it can be used as a homogenous immunoassay.

It should be apparent from the foregoing that there are a number of variations possible within the scope of the invention as disclosed herein. For example, the exciting beam can be polarized and monochromatized and directed to traverse the sample cell from end to end, which typically is a number of times the diameter of the cell, and the sensors can be arranged at the sides of the cell and with a large field of vision, e.g. removing the slits 6 and 10, measuring the polarization fluorescence over all or a substantial area of the long side of the cell, increasing the amount of incident fluorescent light on the photomultipliers several orders of magnitude.

This invention can be used for many determinations by eliminating the time consuming, and that time is rather costly and troublesome and rather critical separation of bound immunological reaction products from unbound immunological reaction, a process which is conventionally required before measuring can be accomplished.

INDUSTRIAL APPLICATION

This invention is useful in conventional diagnostic and scientific immunological reaction measuring processes.

What is claimed is:
1. Apparatus for determining the extent of an immunoreaction by means of fluorescent tagged species, comprising the combination of:
   (a) an excitation light beam source for producing a pulse of high intensity light for exciting fluorescent radiation in such tagged species;

(b) means for positioning a sample in the path of said excitation light beam;
(c) means in the excitation light beam path for polarizing the excitation light beam directed toward the sample position;
(d) means for measuring the intensity of a first fluorescent light beam emitted from the sample in one direction and at a first polarization orientation;
(e) means for measuring the intensity of a second fluorescent light beam emitted from the sample in another direction at a second polarization orientation; and
(f) means for comparing the output of the first measuring means and the second measuring means and reporting the difference between such outputs.

2. The apparatus of claim 1 further including:
a collimator and a monochromator in the path of the excitation light beam;
a collimator and a monochromator in the path of the first fluorescent light beam; and
a collimator and a monochromator in the path of the second fluorescent light beam.

3. Apparatus for determining the extent of an immunoreaction by means of fluorescent tagged species, comprising:
(a) an excitation light beam source for producing a pulse of high intensity light for exciting fluorescent radiation in the tagged species;
(b) means for positioning a sample in the path of said excitation light beam;
(c) means in the excitation light beam path for polarizing the excitation light beam directed toward the sample position;
(d) means for measuring the intensity of a first fluorescent light beam emitted from the sample in a first direction and at a first polarization orientation;
(e) means for measuring the intensity of a second fluorescent light beam emitted from the sample simultaneously with the first beam in another direction at a second polarization orientation;
(f) means connected to said first and second measuring means for comparing the output of the first measuring means and the second measuring means and reporting the difference between said outputs; and
(g) means for selectively disconnecting either one or both of said first and second measuring means from said comparing means.

* * * * *